(12) United States Patent
Kurtz et al.

(10) Patent No.: US 7,743,672 B2
(45) Date of Patent: Jun. 29, 2010

(54) MULTIPLE AXIS LOAD CELL CONTROLLER

(75) Inventors: Anthony D. Kurtz, Saddle River, NJ (US); Adam Kane, Morristown, NJ (US); Richard Martin, Ridgewood, NJ (US); Robert Gardner, Westwood, NJ (US)

(73) Assignee: Kulite Semiconductor Products, Inc., Leonia, NJ (US)

( * ) Notice: Subject to any disclaimer, the term of this patent is extended or adjusted under 35 U.S.C. 154(b) by 89 days.

(21) Appl. No.: 12/157,029

(22) Filed: Jun. 6, 2008

(65) Prior Publication Data

US 2009/0301217 A1    Dec. 10, 2009

(51) Int. Cl.
    *G01D 7/00*    (2006.01)
(52) U.S. Cl. .............................. 73/862.046; 73/862.041
(58) Field of Classification Search ..................
                                      73/862.041–862.046
    See application file for complete search history.

(56) References Cited

U.S. PATENT DOCUMENTS

| | | | | |
|---|---|---|---|---|
| 4,448,083 A | * | 5/1984 | Hayashi | 73/862.042 |
| 4,470,824 A | * | 9/1984 | Huret et al. | 474/195 |
| 4,573,362 A | * | 3/1986 | Amlani | 73/862.045 |
| 4,640,138 A | * | 2/1987 | Meyer et al. | 73/862.045 |
| 5,894,094 A | * | 4/1999 | Kuchler et al. | 73/862.044 |
| 6,038,933 A | * | 3/2000 | Meyer | 73/862.045 |
| 6,777,839 B2 | * | 8/2004 | Casey et al. | 310/68 D |
| 6,799,481 B2 | * | 10/2004 | Nieding et al. | 73/862.338 |

\* cited by examiner

*Primary Examiner*—Max Noori
(74) *Attorney, Agent, or Firm*—Troutman Sanders LLP; James E. Schutz; Bernard G. Pike

(57) ABSTRACT

There is disclosed a multiple axis load cell or controller in which axial and torsion measurements are decoupled while maximizing the outputs of both measurements. The active member of the load cell is a wheel with dual beams as the spokes. The wheel thus has four spokes or four beam members, each spoke is a pair of rectangular cross-section beams, orthogonal to each other. The beams have strain gages on the wide surfaces which measure the bending strain which is proportional to torsion or the axial input. There is an inner beam section and an outer beam section associated with each spoke and orthogonal to each other. The outer beams have the wide surface normal to the axis of the load cell. This beam section is more sensitive to the axial tension/compression input. The inner beam sections have their wide surface parallel to the axis of the load cell and are much less sensitive to bending but are sensitive to torsion. Therefore when a torsion or twisting motion is applied to the load cell, the inner beams with their wide surface parallel to the axis of the wheel are more sensitive and bend more. These beams experience bending as a result of the torsion input and have strain gages formed in a Wheatstone bridge arrangement to provide an output proportional to the torsion. The outer beams also have gages mounted thereon which are also wired in a Wheatstone bridge configuration and which Wheatstone bridge output of these gages are proportional to the axial force.

20 Claims, 4 Drawing Sheets

MULTIPLE AXIS LOAD CELL CONTROLLER

RELATED APPLICATIONS

The applications entitled "Hermetically Sealed Displacement Sensor" filed on Dec. 20, 2005 as Ser. No. 11/322,721 and "Joystick Sensor Apparatus" filed on Jul. 3, 2007 as Ser. No. 11/824,920 are generally related.

FIELD OF THE INVENTION

This invention relates to a multiple axis controller employing load cells and more particularly to a multiple axis load cell in which the axial and torsional measurements are decoupled while maximizing the output of both measurements for use in a controller.

BACKGROUND OF THE INVENTION

Basically a controller is designated as a device which can provide multiple axis outputs, or multiple measurements using load cells. These devices, for example, can be used in fly by wire systems, which require very high reliability, limit and ultimate load, and safety margin. Such fly by wire systems utilize a controller which basically is a multiple axis or multiple measurement load cell, the pilot manipulates the controller by twisting it to the right or the left and moving it up and down. In this manner, a twist to the left would indicate a left turn for the aircraft, a twist to the right would indicate a right turn. The movement up and down, would indicate a pitch or a roll. In any event, such devices are known. These devices are similar to joysticks which basically have an elongated shaft or control rod, which rod or shaft is manipulated in x or y direction and can provide a 360° movement, whereby the sensor produces an output based on the position of the rod. See the above noted co-pending application entitled "Joystick Sensor Apparatus". Joystick sensors have been used for steering controls for helicopters and other aircraft as well as in many other applications. Thus the above noted application entitled "Joystick Sensor Apparatus" is incorporated herein in its entirety.

In any event, this controller employs load cells which are optimized for multiple axis or multiple measurements. The load cell design typically includes maximizing the output of the strain gages while also maximizing the safety factor, especially for flight control load cells. As indicated, flight control load cells are typically used on fly by wire systems, which require very high reliability, limit and ultimate load, and safety margins. In optimizing a load cell for torsion measurement, the axial output on the same beam will be very low. Reversing the design, optimizing for axial tension/compression gage output, results in a much thinner beam, which will fail under torsion conditions. The instrumented devices for an axial-torsion multiple measurement load cell must be decoupled to eliminate this problem. Various schemes for decoupling include two load cells in series. The problem arises, for the design of the axial load cell section, which is typically also exposed to the torsion inputs. The axial section must be designed such that the axial output is adequate, while preventing failure due to torsion.

This has been a serious problem in the prior art as it is desirable to provide a multiple axis load cell in which the axial and torsion measurements are decoupled, while maximizing the output of both measurements and providing adequate robustness and adequate safety margins for the entire structure.

SUMMARY OF THE INVENTION

A controller for providing operation in multiple axes, comprising: a load cell having an outer peripheral frame having a central axis with a central concentric area about said axis, said load cell having beam members positioned between said central area arid said outer peripheral frame, each beam having a first beam section of a rectangular cross section having wide top and bottom surfaces and narrower side surfaces, with said wide surface positioned normal to the axis of said frame, and having a second beam section extending from said first section, said second beam section of a rectangular cross section having wide top and bottom surfaces and narrower side surfaces, with said wide surfaces parallel to the axis of said frame; a plurality of strain gages, with at least one gage positioned on one wide side of said first and second beam sections; a movable member coupled to said central area and operative to apply torsional or axial forces to said central member to cause said first beam section and said associated gage to provide an output proportional to mainly said axial force and to cause said second beam section and said associated gage to provide an output proportional to mainly said torsional force.

BRIEF DESCRIPTION OF THE FIGURES

FIG. 5 consists of FIGS. 5A, 5B and 5C. FIG. 5A is front plan view of a load cell configuration according to this invention. FIG. 5B is a cross-sectional view taken through line B-B of FIG. A, while FIG. 5C is a cross-sectional view taken through A-A of FIG. 5A.

DETAILED DESCRIPTION OF THE FIGURES

Figure 1:
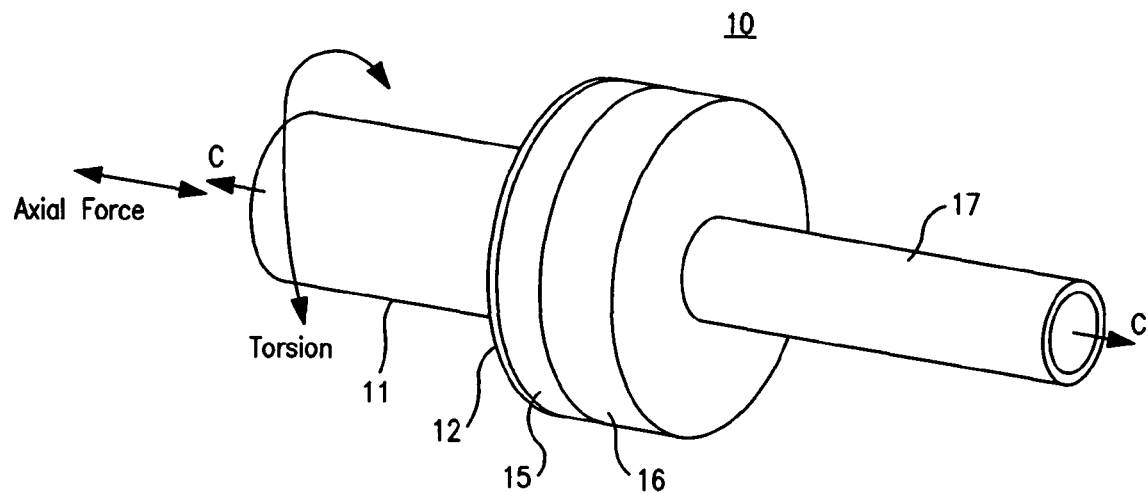
FIG. 1 is a perspective view of a controller according to this invention.

Referring to FIG. 1 there is shown a controller 10 according to this invention. Essentially as indicated above, the term controller is used in lieu of the term joystick as the controller shown in FIG. 1 produces outputs proportional to torsion and outputs proportional to axial forces. As seen in FIG. 1, there is an active end which essentially consists of a cylindrical member 11, which cylindrical member 11 responds to torsion in either a clockwise or counterclockwise direction and cylindrical member 11 may also be moved up and down to create an axial force. Both the torsion and axial forces are responded to by the load cell arrangement as will be explained, and which load cell arrangement produces outputs proportional both to the torsion and to the axial force. As seen, the cylindrical member 11, also designated as a yoke, can accommodate a handle or gripping mechanism to enable a user to twist member 11 to the right or to the left to create a torsional force as shown by the arrows TORSION in FIG. 1, and also to cause the member 11 to move axially AXIAL FORCE. The entire device 10 is symmetrically disposed about a central axis C. Member 11 is associated with a seal 12, with seal 12 interfacing with a wagon wheel assembly 15. The wagon wheel assembly basically contains strain gages or sensor devices and will respond to both torsional and axial forces. The wagon wheel member 15 is covered by a cover member 16 which is associated with a spline adaptor 17, which spline adapter member may be coupled to member 16 or maybe integrally formed therewith. Essentially, as one can see, spline adapter 17 and cover member 16 are mounted on a fixed non-movable surface. The yoke member 11 is then twisted or moved axially to produce outputs from the associated gage members, which outputs are indicative of torsional movement to the right, torsional movement to the left or axial movement downwards or upwards. These electrical signals are produced by the sensor arrangements or gages on the wagon wheel assembly 15 as will be further explained.

Figure 2:
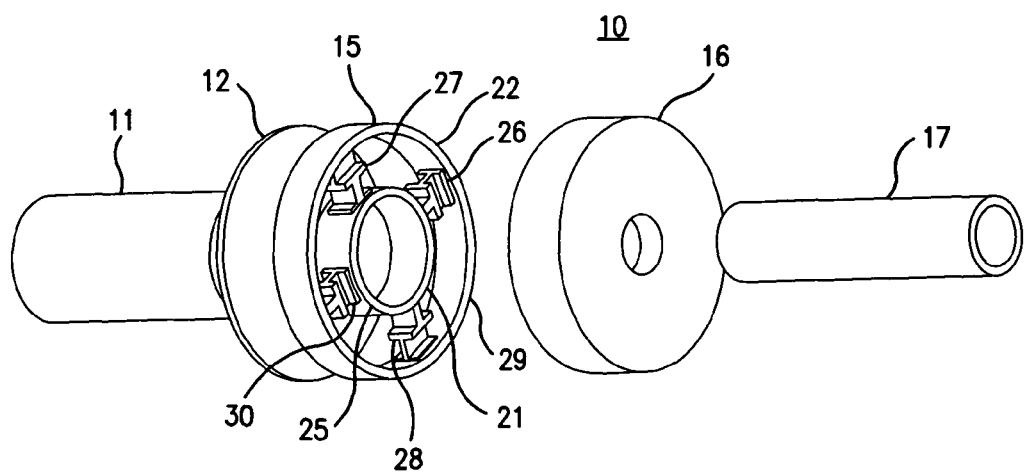
FIG. 2 is an assembly view of the controller of FIG. 1.

Referring to FIG. 2 there is shown an assembly view in perspective of the controller 10 of FIG. 1. As seen, the same reference numerals have been designated to reference similar operating parts. In FIG. 2 there is shown the wagon wheel assembly 15, and hence, one can understand from looking at the configuration why it is designated as a wagon wheel. Essentially the assembly 15 is a multi axis load cell in which the axial and torsional measurements are decoupled. This decoupling occurs while one maximizes the output of both measurements and provides a strong and robust structure with a large safety margin. The active member of the load cell or controller is the wagon wheel structure 15 which has dual beams as the spokes, for example, beams 25 and 26, as well as beams 27 and 28. Each beam extends from an outer frame member 29 to an inner coaxial member 30, thus providing the shown structure. As indicated, the wagon wheel 15 employing the dual beams as the spokes is the main active member of this invention. Each spoke such as 25 and 26 and 27 and 28, is a pair of rectangular cross-section beams, orthogonal to each other. In operation the beams are in bending, with the strain gage or gages on the wide surfaces, measuring the bending strain, which is proportional to the torsion or axial input. As one will see, each of the beams is associated with strain gages on the wide surface. These gages measure the bending strain, as indicated, which is proportional to the torsion or axial input.

Figure 3:
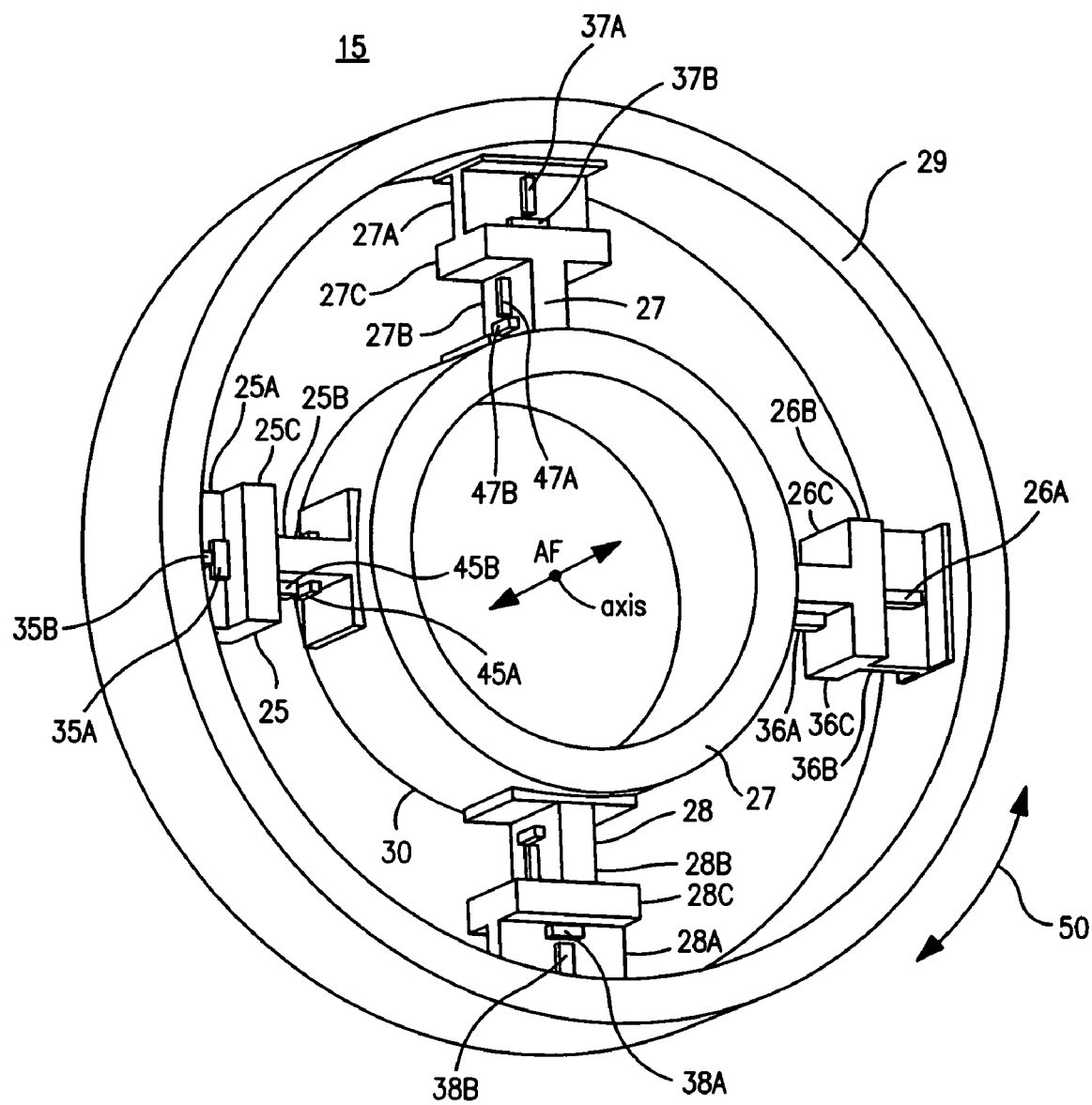
FIG. 3 is a perspective view of a load cell having a wheel like construction and employing dual beams as the spokes.

Referring to FIG. 3 there is shown a detailed diagram of the wagon wheel structure 15 of FIG. 2. There is shown beams 27 and 28, which beams are located on the same diameter with respect to the outer frame member 29. Beams 25 and 26 are also located on the same diameter and are relatively transverse to beams 27 and 28. Each of the beams has an upper "A" section as 27A and a lower B section as 27B. The sections, 27A and 27B all emanate from a common central base C section as 27C. Thus each beam as 25, 26 and 28 has a top section designated by the letter A, a bottom section designated by the letter B, with a base or planar section designated by the letter C. Thus beam 26 has top section 26A which emanates from the base section 26C with a bottom section 26B. The outer beams, as the A beams, have the wide surface normal to the axis of the wheel. These beams are active and more sensitive to the axial tension/compression input. With an axial force applied to the center ring 30, such as shown by arrow AF, which is along the central axis of the controller 20 as shown in FIG. 1 and the axis of the wheel, the A beam sections respond. With the axial force applied to the center ring 30 and the outer ring 29 fixed the outer beams A will bend. This bending imparts a strain on the wide beam surface. This strain is measured by the gage arrangements as 37A and 37B, both of which are located on the wide surface of the beam 27. The strain gages may be piezoresistors which are semiconductor devices or can be wire or other type gages although piezoresistors are preferred. It is also noted and not shown, but the same arrangement of the two sensors as 37A and 37B are also on the wide backside of the beam 27A, thus each of the beams have a top pair of sensors as 37A and 37B for beam 27. Thus beam 25 has top pair of sensors 35A and 35B while beam 28A has a top pair of sensors as 38A and 38C and so on. Each beam also has a bottom pair of sensors on the wide surface which is parallel to the axis of the wheel or cylinder. Thus beam 27 has a pair of sensors 47A and 47B on the bottom section 27B of the beam. There are also two sensors as $47B^1$ and $47A^1$ on the opposite side of the bottom section 27B. Thus each beam has basically 8 sensors, two on each side. The sensors are on the corresponding opposite surfaces of each beam. Sensors as 37A and 37B can be wired to the corresponding sensors on the other side to form a Wheatstone bridge. In any event, the sensors 37A and 37B can also be wired with sensors 38A and 38B to form a Wheatstone bridge as well. As seen, these sensors basically bend when a force is applied such as AF. The sensors shown are arranged transverse to each other which is basically designated as a Poisson gage arrangement. In any event, apart from the Poisson arrangement employed, one can use the sensors or arrange the sensors in a bending arrangement instead of in a Poisson arrangement. The Wheatstone bridge thus formed by the output of these gages will provide an output proportional to the axial force AF. Thus, as one can see, the outer beams which have their wide surface normal to the axis of the wheel which are designated as the A beams are active and sensitive to the axial force up and down. The inner beams have their wide surface parallel to the axis of the cylinder parallel to the axis of the wheel, are much less sensitive to bending. Their section modulus is much greater as their long dimension is along the bending axis. Thus when a torsion or twisting movement designated by arrow 50 is applied to the inner ring 30 with the outer ring 29 fixed, the inner set of beams B, with their wide surface along the axis of the wheel are more sensitive. These B beams, such as 27B, 26B, 28B and 25B also experience bending as a result of the torsion input and have the Poisson gages in a Wheatstone bridge arrangement to provide a voltage output proportional to the tension. Although the gages are shown as Poisson, they can be placed in any convenient manner, such as tension/compression or bending. While the inner B beams are more sensitive to torsion, the outer A beams, with their wide surface normal to the axis of the wheel, are far less sensitive to the torsion. Their section modulus, with respect to the torsion input is much greater, as the critical dimension for section modulus in that direction is much greater. Thus by using orthogonal beams as 27A and 27B, with the sensitivities optimized for bending as a result of torsion or tension/compression, the measurements are decoupled. This high torsion input will not affect the tension/compression beam or the A beams, because it is much stiffer and thus more resistant in the bending directions as a result of the twist of the inner ring 30. In a similar fashion, the bending beams with their long dimension in the plane of the twisting input are not affected and are less sensitive to torsion inputs making them more robust. With the dual orthogonal bending beam, such as 27A and 27B and its companion 28 and beam 25 and its companion 26, the outputs of both torsion and tension/compression can be maximized, without sacrificing safety, which is extremely important for flight control/fly by wire devices.

The relative sensitivity of the beams, to minimize crosstalk, can be determined from their section modulus.

Typically, beam stiffness K is $$K = 3EI/L^3$$

Where
E=modulus of elasticity
I=section modulus
L=length
The ratio of stiffness of one beam to the other is $$K_1/K_2 = E_1 I_1 L_2^3 / E_2 I_2 L_1^3$$

For a rectangular beam in general, $$I = bh^3/12$$

Where
b=width
h=thickness (in bending direction)

Both beams are of the same material, and the same length. For beams with like width and thickness dimension, just orthogonal to each other, we have $$K1/K_2 = I1/I_2 = bh^3/hb^3 = h^2/b^2 = (h/b)^2$$

For a beam with a 5 to 1 width to thickness ratio, we have $$K_1/K_2 = (1/5)^2 = 0.04$$

Or inversely, $$K_2/K1 = 25$$

Thus the sensitivity to bending versus torsion is 25 to 1.

As indicated, each beam section as A and B have a rectangular cross-section. The rectangle has wide sides and narrow sides. The wide sides are longer than the narrow sides and may be four or more times longer. While the A and B beam sections bend they bend more according to the type of force. Thus, as indicated, the A sections bend more for axial forces, while the B sections bend more for torsional forces. However there is "crosstalk" which means that the A sections will also bend for torsional forces and the B sections for axial forces. By adjusting the length of the wide side of the rectangle to the length of the narrow side, "crosstalk" can be minimized to less than 4%. Further, by strategic placement of the gages, crosstalk can be further minimized or cancelled out. In addition, the axial direction can be stopped from overload by designing a gap between the inner ring of the wheel and cover or seal member. This stop is similar to a over pressure stop on the silicon diaphragm with the gap between the boss and pedestal glass. Thus as seen in FIG. 3 and as can be understood, by using the orthogonal beams, with the sensitivities optimized for bending as a result of torsion or tension/compression, the measurements of the axial forces and forces due to torsion are decoupled. Thus large torsion inputs do not affect the tension/compression beam because it is much stiffer, and thus more resistant in the bending direction as a result of the twist of the inner ring. In a similar fashion, the bending beams with their long dimension in the plane of the twisting input are not affected and are less sensitive to torsion inputs making them more robust.

Figure 4:
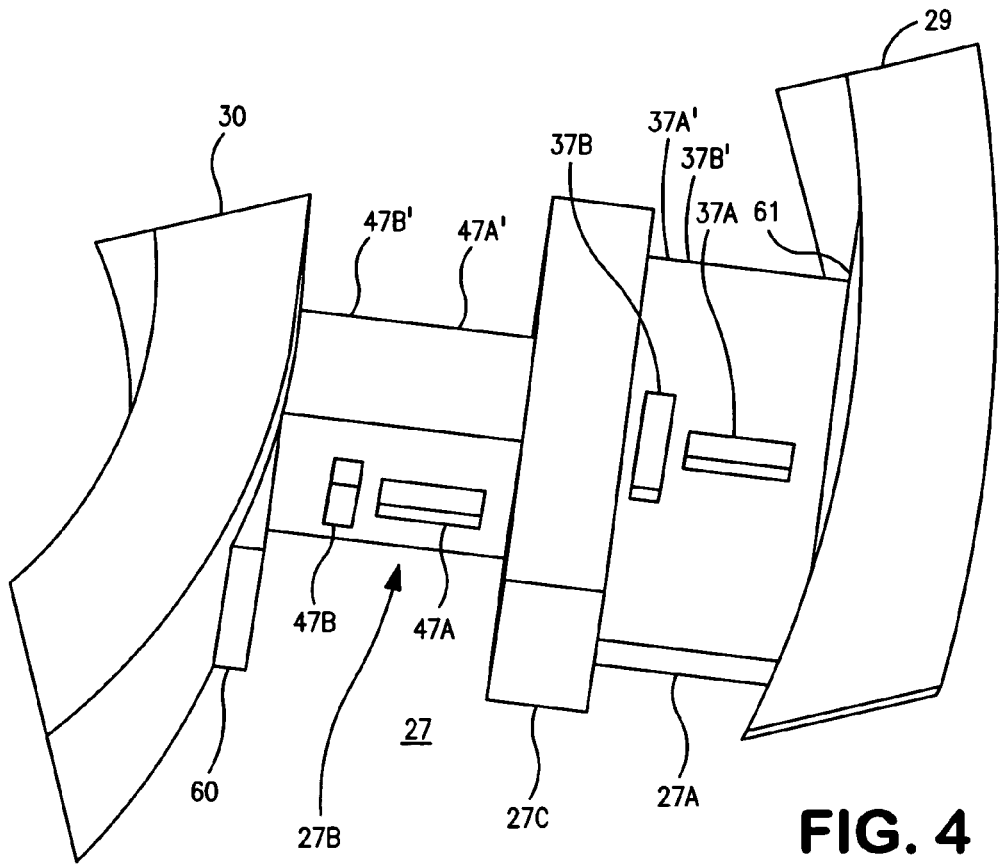
FIG. 4 is a partial cross-sectional view showing a single beam with sensors mounted thereon.

Referring to FIG. 4 there is shown a partial sectional view depicting the beam 27 of FIG. 3 to show more clearly the nature of the structure. As seen, the entire beam consisting of sections 27A, 27B and 27C is positioned on a diameter of the outer frame 29 and between the inner concentric member 30 and outer frame 29. The beam has an end 60 which has an arcuate top surface so that it can be secured to member 30. The beam has a top section 27A which top beam section 27A also designated as the outer beam, has the wide surface normal to the axis of the cylinder or wheel and is active and more sensitive to the axial tension/compression input. With the axial force applied to the center ring 30 and the outer ring held 29 fixed, the outer A beam will bend imparting a strain on the wide beam surface which is measured by the Poisson gage arrangement. The wide beam section 27A has gages 37A and 37B on the wide surface and which gages are arranged transverse to each other. There are also gages $37A^1$ and $37B^1$ on the opposite surface on beam section 27 (not shown). Hence the beam section 27A has two gages on the top surface as shown as gages 37A and 37B and two gages on the opposite surface designated as $37A^1$ and $37B^1$. The beam section 27A extends from the periphery of the outer ring 29 to the separation or planar base member 27C. Extending from base member 27C is the beam section 27B. The beam section 27B also has gages 47A and 47B on one surface and gages $47A^1$ and $47B^1$ on the opposite surface (not shown). Gages 37A, 37B and $37A^1$ and $37B^1$ can be wired in a Wheatstone bridge configuration or gages on opposite beams on the same diameter, can be wired to also form a Wheatstone bridge array and this can occur for the top section 27A as well as for the bottom section 27B with top section 28A and bottom section 28B of beam 28. Other arrangements are also possible.

Figures 5A, 5B, 5C:
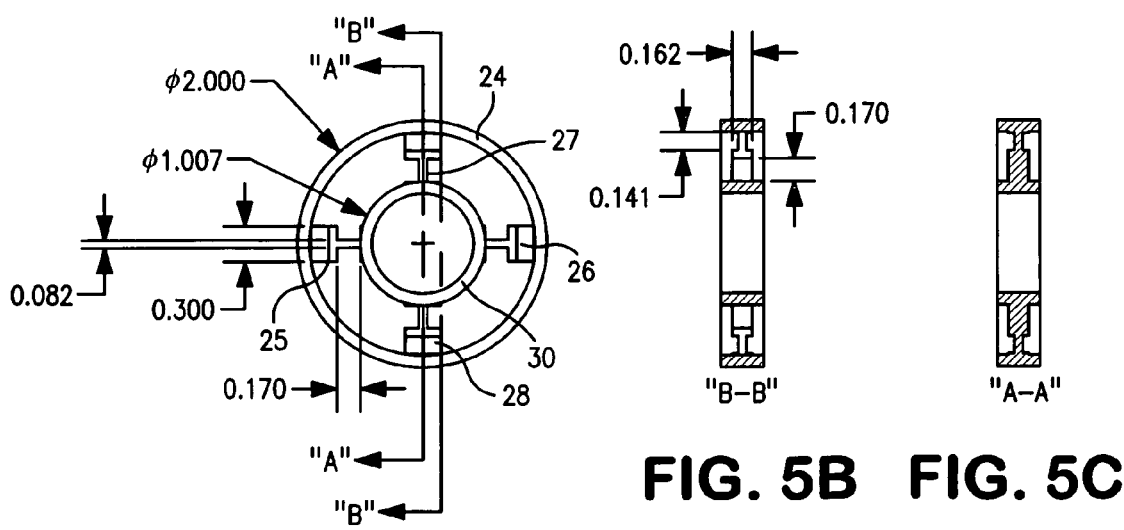

Referring to FIG. 5 there is shown in FIGS. 5A, 5B and 5C typical dimensions of the wagon wheel load cell described in conjunction with the above. Thus FIG. 5A shows that the outer ring or frame 29 is 2 inches in diameter while the inner concentric ring 30 is 1.007 inches in diameter. There is a section taken through line A-A of FIG. A which section is shown as FIG. 5C as well as a section taken through B-B of FIG. A which is shown in FIG. 5B. Thus it is seen that the width of the top section A is 0.3 inches while the width of the bottom section B as shown in FIG. 3 is 0.082 inches, whereby section A is approximately 4 times larger than section A looking at the front view of FIG. 5A. Other dimensions can be discerned as well from the dimensions given in FIG. 5. Dimensions are examples and representative of structure, and are optimized for loads to be controlled or measured. These dimensions are given by way of example.

Figure 6:
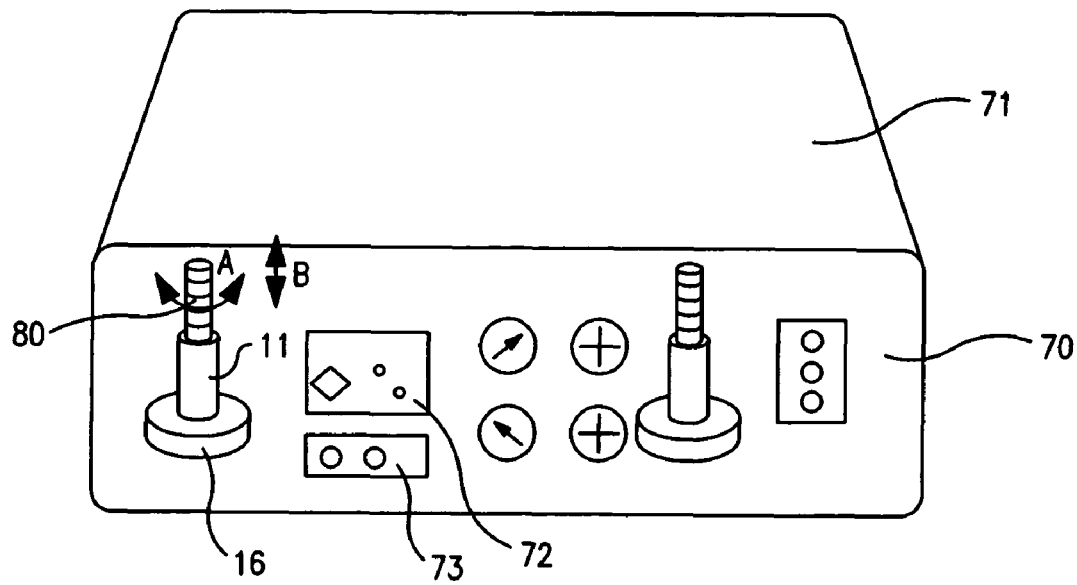
FIG. 6 is a front view of a console such as an aircraft dashboard employing the controller according to this invention.

Referring to FIG. 6 there is shown a typical use for the controller or load cell apparatus depicted above. As one can see, the apparatus would be placed on a console 70 which may be the console of an aircraft having a viewing window 71 and various instrument indicators as 72 as well as control buttons and knobs 73. The panel shown in FIG. 6 is fictitious and shown purely for explanation purposes. In any event, the controller mechanism is shown mounted on the console or dashboard 70 of the vehicle to be controlled. There is a handle 80 which is coupled to the cylindrical member 11 whereby the cover member or base 16 is firmly secured to the console and where the associated spline adapter 17 is fixed. In any event, the handle 80 is manipulated in the direction of the arrows A and B to show torsional and axial forces being imparted. A twisting or force in the direction of arrow A to the right, clockwise will cause the aircraft to go to the right while a counterclockwise torque will cause the aircraft to go to the left. A push or pull up will cause the aircraft to rise while a pull or push down will cause the aircraft to descend. This as indicated can be used in a fly by wire system whereby electrical signals are used to control the aircraft such as controlling the air foils or other parts of the aircraft which eliminates mechanical links from the controls.

Referring back to FIG. 2, it is seen that the cover member 16 is welded to the outer member 29 as shown in FIG. 1. Therefore, since the cover member and associated spline 17 are fixed, the outer ring 29 is fixed. The seal 12 is then welded to the inner ring 30 by means of a laser weld, and therefore the inner ring 30 will respond to torsion or to axial forces while the outer ring 29 remains stationary since the outer ring is welded to the cover member which is stationary.

Figure 7A:
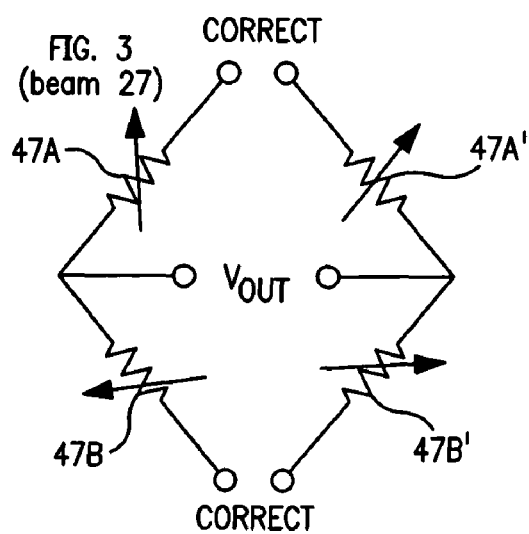
FIG. 7A shows a Wheatstone bridge configuration which is formed from the sensors associated with the controller design according to this invention.
Figure 7B:
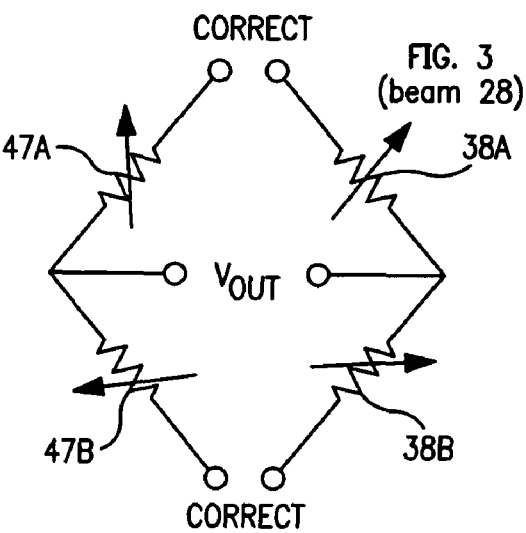
FIG. 7B shows another Wheatstone bridge configuration which can also be provided by the sensors employed with this invention.

Referring to FIGS. 7A and 7B there is shown two Wheatstone bridges whereby such bridges can be formed from the piezoresistors on both sides of the beam such as piezoresistors 47A, 47B, $47B^1$ and $47A^1$ as shown in FIG. A or can be formed from resistors of companion beams such as two resistors from beam 25, two resistors from beam 26, two resistors from beam 28 or two resistors from beam 27 and so on. Thus as one can see, there are numerous configurations available which will measure axial stress or torsional stress and measure such stresses in a reliable and accurate manner. Thus there has been described a multiple axis load cell or controller in which the axial and torsion measurements are decoupled. The load cell maximizes the output of both measurements while providing adequate strength and a good safety margin in the entire structure. As seen that the load cell is compact and as shown in FIG. 1 is basically and symmetrically disposed along a central axis C as shown in FIG. 1. While the wagon wheel is shown having an outer circular design and an inner circular design, it is noted that other geometrical configurations can be employed as well and all such deviations or alternate embodiments are deemed to be encompassed within the spirit and scope of the claims appended hereto.

What is claimed is:

1. A controller for providing operation in multiple axes, comprising:
   a load cell having an outer peripheral frame having a central axis with a central concentric area about said axis, said load cell having a plurality of pairs of a first beam section and a second beam section positioned between said central area and said outer peripheral frame, each beam section having an elongated rectangular cross-section,
   wherein the first beam section has wide top and bottom surfaces and narrower side surfaces, with said wide surface of said first beam section are positioned normal to the axis of said frame, and the second beam section extends from said first section, said second beam section having wide top and bottom surfaces and narrower side surfaces, with said wide surfaces of said second beam section are parallel to the axis of said frame;
   a plurality of strain gages, with at least one gage positioned on one wide side of said first beam section and at least one gage positioned on said wide side of said second beam section;
   a movable member coupled to said central area and operative to apply torsional or axial forces to said central member to cause said first beam sections and said associated gages to provide an output proportional to mainly said axial force and to cause said second beam sections and said associated gages to provide an output proportional to mainly said torsional force.

2. The controller according to claim 1 wherein said outer peripheral frame is a circular frame, with a central circular concentric area.

3. The controller according to claim 2 having four beams with one pair located along a first diameter of said frame and with a second pair located along a second diameter of said frame.

4. The controller according to claim 3 wherein said first beam section has one end coupled to said frame and the other end coupled to an end of said second beam section, with the other end of said second section coupled to said central area.

5. The controller according to claim 4 wherein said top wide surfaces of each of said first and second beam sections has at least two strain gages mounted thereon.

6. The controller according to claim 5 wherein two gages from one beam section are connected to two gages from the same beam section of the same beam pair to form a Wheatstone bridge.

7. The controller according to claim 5 wherein said wide bottom surface of said beam sections also have two strain gages mounted thereon.

8. The controller according to claim 7 wherein two gages from a top surface of a first beam section are connected to two gages on said bottom surface of the same beam section to form a Wheatstone bridge.

9. The controller according to claim 5 wherein said two gages are Poisson gages.

10. The controller according to claim 9 wherein said gages are piezoresistors.

11. The controller according to claim 1 further comprising:
    means coupled to said outer peripheral frame to hold the same in a fixed position with respect to said central concentric area.

12. The controller according to claim 11 further comprising:
    means coupled to said central concentric area to provide both torsional and axial forces to said central area.

13. The controller according to claim 12 wherein said means is a control rod connected to said central area.

14. A multiple axis load cell comprising:
    a wheel having an outer circular frame and an inner concentric central area, the wheel having a radial direction and an axis in an axial direction;
    a plurality of spokes located between the outer frame and the inner central area, each spoke including a pair of rectangular cross-sectional beams, wherein each beam has an elongated rectangular cross-section including a length longer than its width as viewed in the radial direction, with said pair of beams orthogonal to each other as viewed in the radial direction, with one beam of said pair having the length normal to the axis of said wheel, with the other beam of said pair having the length parallel to the axis of said wheel, each beam having at least one strain gage mounted on a wide surface defined by said length and a radial height of the beam; and
    means for applying a force to said inner central area whereby for an applied axial force said beams having said length normal to the axis of said wheel bend to cause said associated gage to provide an output proportional to said axial force and whereby for an applied torsional force said beams having said length parallel to said axis of said wheel bend to cause said associated gage to provide an output proportional to said torsional force.

15. The multiple axis load cell according to claim 14 wherein said length is at least 3 times longer than said width for each of said pair of beams of the plurality of spokes.

16. The multiple axis load cell according to claim 14 wherein each beam comprises a radial height and wherein the radial height and said length define the wide surface and each wide surface has at least two strain gages mounted thereon.

17. The multiple axis load cell according to claim 16 wherein said strain gages are Poisson gages.

18. The multiple axis load cell according to claim 14 further including means for connecting said strain gages in a bridge circuit.

19. The controller according to claim 1, wherein neither said first beam section nor said second beam section have a gage positioned on the narrower side surfaces.

20. The multiple axis load cell according to claim 14, wherein each beam comprises a radial height and wherein the radial height and said width define a narrow surface and each narrow surface does not comprise a strain gage mounted thereon.

* * * * *